US00RE37298E

(19) United States
(12) Reissued Patent
Volk

(10) Patent Number: US RE37,298 E
(45) Date of Reissued Patent: Jul. 31, 2001

(54) INDIRECT OPHTHALMOSCOPY LENS RETAINING RING

(75) Inventor: Donald A. Volk, Mentor, OH (US)

(73) Assignee: Volk Optical, Inc., Mentor, OH (US)

(21) Appl. No.: 29/042,668

(22) Filed: Aug. 14, 1995

Related U.S. Patent Documents

Reissue of:

(64) Patent No.: Des. 357,319
Issued: Apr. 11, 1995
Appl. No.: 29/015,401
Filed: Nov. 15, 1993

U.S. Applications:

(63) Continuation of application No. 08/131,086, filed on Oct. 1, 1993, now Pat. No. 5,430,506.

(51) LOC (7) Cl. ..... 24-01
(52) U.S. Cl. ..... D24/172
(58) Field of Search ..... D24/172; 351/205, 351/206, 219; 359/708, 712

(56) References Cited

U.S. PATENT DOCUMENTS 3,944,341 3/1976 Pomerantzeff .
4,913,545 * 4/1990 Volk ..... 351/205
4,934,809 * 6/1990 Volk ..... 351/205
5,046,836 9/1991 Volk .
5,255,025 * 10/1993 Volk ..... 351/205

* cited by examiner

*Primary Examiner*—Stella Reid
(74) *Attorney, Agent, or Firm*—Venable; Robert Kinberg

(57) CLAIM

The ornamental design for an indirect ophthalmoscopy lens retaining ring, as shown and described.

DESCRIPTION

Figure 1:
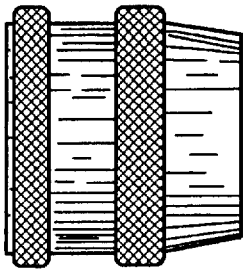
FIG. 1 is a side elevational view of an indirect opthalmoscopy lens retaining ring, showing my new design.
Figure 2:
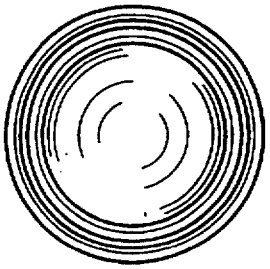
[FIG. 2 is a cross-sectional view taken along lines 2—2 of FIG. 1;]
Figure 3:
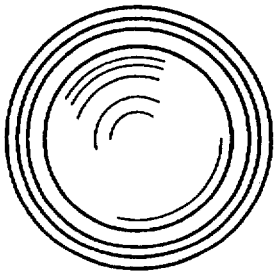

FIG. [3] *2* is an end elevational view taken from the left of FIG. 1 and;

FIG. [4] *3* is an end elevational view taken from the right of FIG. 1.

1 Claim, 1 Drawing Sheet

Matter enclosed in heavy brackets [ ] appears in the original patent, but forms no part of this reissue; matter printed in italics indicates the additions made by reissue.